United States Patent [19]

Waterhouse et al.

[11] Patent Number: 5,710,628
[45] Date of Patent: Jan. 20, 1998

[54] AUTOMATED ELECTROPHORESIS AND FLUORESCENCE DETECTION APPARATUS AND METHOD

[75] Inventors: Paul Waterhouse, Copetown; John A. Renfrew, Burlingon; John K. Stevens, Toronto, all of Canada

[73] Assignee: Visible Genetics Inc., Toronto, Canada

[21] Appl. No.: 353,932

[22] Filed: Dec. 12, 1994

[51] Int. Cl.$^6$ ................................................ G01N 21/00
[52] U.S. Cl. .................... 356/344; 204/461; 204/466; 204/612
[58] Field of Search .................... 356/344, 318, 356/376, 335; 204/461, 466, 467, 612, 616, 618

[56] References Cited

U.S. PATENT DOCUMENTS

| | | | |
|---|---|---|---|
| 3,916,197 | 10/1975 | Fulwyler | 356/335 |
| 4,329,591 | 5/1982 | Fujiwara et al. | 250/548 |
| 4,343,991 | 8/1982 | Fumiwara et al. | 250/227 |
| 4,729,947 | 3/1988 | Middendorf et al. | 435/6 |
| 4,811,218 | 3/1989 | Hunkapiller | 364/413.01 |
| 4,823,007 | 4/1989 | Hanson | 250/327.2 |
| 4,832,815 | 5/1989 | Kambara et al. | 204/299 R |
| 4,881,812 | 11/1989 | Ohkubo et al. | 356/344 |
| 4,927,265 | 5/1990 | Brownlee | 356/73 |
| 4,930,893 | 6/1990 | Manian | 356/344 |
| 4,960,999 | 10/1990 | McKean et al. | 250/461.1 |
| 4,981,977 | 1/1991 | Southwick et al. | 548/455 |
| 5,006,210 | 4/1991 | Yeung et al. | 204/180.1 |
| 5,045,172 | 9/1991 | Guzman | 204/299 R |
| 5,051,162 | 9/1991 | Kambara et al. | 204/299 R |
| 5,062,942 | 11/1991 | Kambara et al. | 204/299 R |
| 5,069,769 | 12/1991 | Fujimiya et al. | 204/182.8 |
| 5,091,652 | 2/1992 | Mathies et al. | 250/458.1 |
| 5,100,529 | 3/1992 | Fuji | 204/299 R |
| 5,108,179 | 4/1992 | Myers | 356/344 |
| 5,119,316 | 6/1992 | Dam et al. | 364/498 |
| 5,122,345 | 6/1992 | Tabor et al. | 422/116 |
| 5,162,654 | 11/1992 | Kostichka et al. | 250/458.1 |
| 5,171,534 | 12/1992 | Smith et al. | 422/82.05 |
| 5,190,632 | 3/1993 | Fujiyama et al. | 204/299 R |

(List continued on next page.)

FOREIGN PATENT DOCUMENTS

| | | |
|---|---|---|
| 454286 | 10/1991 | European Pat. Off. . |
| 0483460 | 6/1992 | European Pat. Off. . |
| 0592060 | 4/1994 | European Pat. Off. . |
| 2411361 | 9/1975 | Germany . |
| 87/07719 | 11/1987 | WIPO . |
| 94/03631 | 2/1994 | WIPO . |

OTHER PUBLICATIONS

Hjerten, S., "Free zone electrophoresis" in *Chromatographic Reviews* 9: 122–219 (1967).

Smith et al., "Sequence Detection in Automated DNA Analysis," *Nature* 321: 674–679 (1986).

*Primary Examiner*—Frank G. Font
*Assistant Examiner*—Robert Kim
*Attorney, Agent, or Firm*—Oppedahl & Larson

[57] ABSTRACT

Improved detection methods and apparatus which may be used individually or in various combinations enhance the ability of the electrophoresis apparatus to detect fluorophore-labeled materials in short periods of time. One such apparatus comprises a housing adapted to receive an electrophoresis gel holder; an excitation source of electromagnetic radiation having a frequency effective to induce emission of electromagnetic radiation from the fluorophore; a plurality of optical fibers for delivering electromagnetic radiation from the excitation source to a linear array of excitation/detection sites on the gel holder, optical switching means for sequentially directing electromagnetic radiation into one of several pre-defined groups of the optical fibers; detection means such as a photomultiplier tube, or an array of photomultiplier tubes for detecting emission from the fluorophore induced by a radiation from the excitation source; and means for correlating a detected emission with the switching of the excitation electromagnetic radiation such that a given emission may be linked with the excitation/detection site being irradiated.

15 Claims, 10 Drawing Sheets

U.S. PATENT DOCUMENTS

| | | | |
|---|---|---|---|
| 5,207,880 | 5/1993 | Middendorf | 204/182.2 |
| 5,208,466 | 5/1993 | Pentoney, Jr. | 250/574 |
| 5,213,673 | 5/1993 | Fujiyama et al. | 204/299 R |
| 5,230,781 | 7/1993 | Middendorf et al. | 204/182.2 |
| 5,242,567 | 9/1993 | Fujiyama et al. | 204/299 R |
| 5,246,866 | 9/1993 | Nasu et al. | 436/94 |
| 5,268,486 | 12/1993 | Waggoner et al. | 548/427 |
| 5,274,240 | 12/1993 | Mathies | 250/458.1 |
| 5,290,419 | 3/1994 | Kambara et al. | 204/299 R |
| 5,294,323 | 3/1994 | Togusari et al. | 204/299 R |
| 5,307,148 | 4/1994 | Kambara et al. | 356/344 |
| 5,314,602 | 5/1994 | Kambara et al. | 204/299 R |
| 5,324,401 | 6/1994 | Yeung et al. | 204/180.1 |
| 5,360,523 | 11/1994 | Middendorf et al. | 204/182.2 |
| 5,365,455 | 11/1994 | Tibbetts et al. | 364/497 |
| 5,410,412 | 4/1995 | Gombocz et al. | 356/417 |
| 5,419,825 | 5/1995 | Fujii | 204/299 |
| 5,420,691 | 5/1995 | Kawaguchi | 356/375 |
| 5,439,578 | 8/1995 | Douichi et al. | 356/344 |
| 5,534,125 | 7/1996 | Middendorf et al. | 204/612 |

AUTOMATED ELECTROPHORESIS AND FLUORESCENCE DETECTION APPARATUS AND METHOD

BACKGROUND OF THE INVENTION

This application relates to a method and apparatus for rapid gel electrophoresis and fluorescence detection of a complex mixture of fluorophore labeled proteins or nucleic acids.

Polyacrylamide gel electrophoresis (PAGE) separation of organic molecules is now routinely performed. *Current Protocols in Molecular Biology*, Chap. 10, John Wiley & Sons (1994). A polyacrylamide gel provides a suitably insoluble sieve so as to permit the separation of organic molecules in solution by size and conformation as they are drawn through the sieve under electromotive force. Such separation of organic molecules provides valuable insights into their structures and functions. For example, PAGE separation can separate two polypeptides of the same size but of different isoforms or polypeptides only 100 daltons difference in size (Current Protocols, 1994). Another use for PAGE is in separation of nucleic acids based on size of fragments, such as in the extremely important application of DNA sequence determination. Maniatis, *Molecular Cloning, A Laboratory Manual*, 2nd ed., 1987.

When the electrophoresed molecules are labeled with a detectable signal, it is possible to detect the separations of molecules in real time. Since the first description of a real-time nucleic acid separation method and apparatus by Smith et al., Sequence Detection in Automated DNA Sequence Analysis", *Nature* 321:674–679 (1986), the technology for so-called Automated DNA sequencing has expanded rapidly. Several automated DNA sequencing apparatuses are commercially available. Methods and apparatus for sequencing of DNA are described in U.S. Pat. Nos. 4,811,218; 4,881,812; 5,062,942; 5,091,652; 5,108,179; 5,122,345; 5,162,654; 5,171,534; 5,190,632; 5,207,880; 5,213,673; 5,230,781; 5,242,567; 5,290,419; 5,294,323; 5,307,148; 5,314,602; 5,324,401; and 5,360,523 which are incorporated herein by reference.

Unfortunately, the existing apparatuses are inadequate for use of PAGE for emerging clinical diagnostic purposes such as diagnostic DNA sequence and fragment analysis. For clinical diagnostic DNA analysis, it is desirable to examine hundreds of complex DNA samples per day. Existing technology does not provide for such capacity. For example, operation of a typical Automated DNA sequencer to evaluate at most about 10 samples requires that a skilled technician spend up to four hours constructing a gel holder, filling the gel holder with actively polymerizing acrylamide solution, inserting a well-forming comb before substantial polymerization has occurred, and waiting for the gel to polymerize (see Maniatis, 1987). Using the gel is equally time consuming. Existing technologies use low density electric fields (less than 100 volts/cm) requiring sample running times of up to four hours. It would be advantageous to have an improved apparatus with improved sample throughput for real-time DNA analysis particularly for use in clinical diagnostic applications.

It is an object of this invention to provide a gel electrophoresis and fluorescence detection apparatus suitable for high throughput clinical diagnostic DNA and protein analysis.

It is a further object of the present invention to provide an electrophoresis apparatus which is capable of using gels which use a high density electric field of 100–400 v/cm.

It is a further object of the invention to provide improved optical excitation and detection techniques for real time detection of fluorescently labeled DNA or protein samples in an electrophoresis gel.

SUMMARY OF THE INVENTION

The present invention achieves these and other objects by providing improved detection methods and apparatus which may be used individually or in various combinations to enhance the ability of the electrophoresis apparatus to detect fluorophore-labeled materials in short periods of time. Thus, one embodiment of the present invention is an apparatus for electrophoretic separation and detection of a sample labeled with a fluorophore comprising:

(a) a housing adapted to receive an electrophoresis gel holder;

(b) an excitation source of electromagnetic radiation having a frequency effective to induce emission of electromagnetic radiation from the fluorophore;

(c) a plurality of optical fibers for delivering electromagnetic radiation from the excitation source to a linear array of excitation/detection sites on the gel holder, (d) optical switching means for sequentially directing electromagnetic radiation into one of several predefined groups of the optical fibers;

(e) detection means such as a photomultiplier tube, or an array of photomultiplier tubes for detecting emission from the fluorophore induced by a radiation from the excitation source; and (f) means for correlating a detected emission with the switching of the excitation electromagnetic radiation such that a given emission may be linked with the excitation/ detection site being irradiated. For example, the optical switching means may alternate between directing radiation from the source into every other optical fiber, or may provide radiation in rotation to every third or fourth fiber.

An alternative embodiment of the invention is an apparatus comprising:

(a) a housing adapted to receive an electrophoresis gel holder loaded with the sample;

(b) a spot array generation grating for dividing an incident beam of coherent radiation of a frequency suitable for excitation of the fluorophore into an array of excitation beamlets and directing each excitation beamlet to an excitation/ detection site on the electrophoresis gel, and (c) a detector, for example a photodiode, for detecting emissions from the excitation/detection site.

A third embodiment of the invention is an apparatus comprising (a) a housing adapted to receive an electrophoresis gel holder;

(b) at least one light emitting diode disposed to deliver excitation energy of a frequency suitable for excitation of the fluorophore to an array of excitation/detection sites on the gel holder, and (c) a detector, for example a photodiode, for detecting emissions from the array of excitation/detection sites due to the low costs of light emitting diodes (LEDs) compared to This latter form of the apparatus is particularly advantageous coherent light sources (e.g. lasers).

DETAILED DESCRIPTION OF THE INVENTION

This application discloses a method and apparatus for rapid gel electrophoresis and real-time fluorescence detection of a complex mixture of fluorophore-labeled organic molecules.

Figure 1:
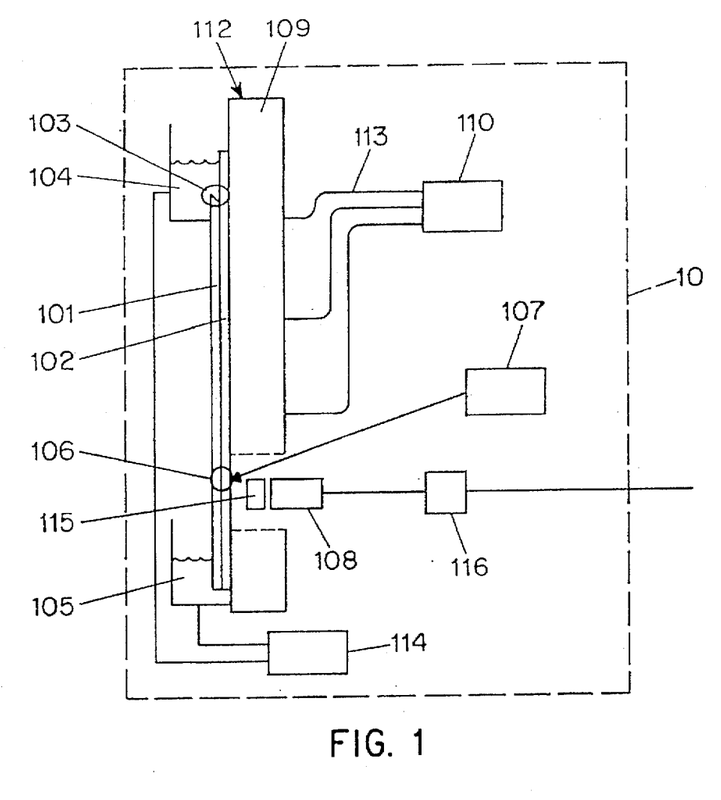
FIG. 1 shows a sectional side view of an apparatus according to the invention.

FIG. 1 shows a sectional side view of an apparatus in accordance with the present invention. The apparatus has a housing 10 within which the means for electrophoretic separation and detection of the sample are disposed. The housing 10 advantageously provides a sealed, light tight environment in which the processing of the sample is conducted.

Within the housing 10, a loaded electrophoresis gel 102 within a gel holder 101 is positioned on a mounting plate 109. The loaded gel is advantageously held in place using suction through the mounting plate 109 generated using suction pump 110 and tubing 113, although other methods of holding the loaded gel in place may be used without departing from the spirit and scope of the invention.

Opposing ends of the loaded gel 102 are placed in contact with two electrodes, such as solution electrodes 104 and 105. These electrodes are connected to a power supply 114 which generates an electric field within the gel. This field causes the sample to migrate in the gel from loading site 103 towards detection site 106.

An excitation source 107 which supplies electromagnetic radiation having a frequency effective to excite the fluorophore used as a label is disposed within the housing 10 such that radiation from the excitation source 107 strikes the gel holder 101 at the detection site 106 causing any fluorophore labeled molecules at the detection site to emit light. This light is collected using optical system 115 and detected using detector 108. The analog output signal from detector 108 may then be converted to a digital signal using an A-to-D converter 116, and output for further processing and/or display.

The apparatus of the invention may be used with any type of electrophoresis gel and gel holder. Preferably, however, the apparatus is used with an ultrathin electrophoresis gel having a thickness of 25–250 microns of the type disclosed and claimed in commonly assigned U.S. patent application Ser. No. 08/332,577 which is incorporated herein by reference. Using such gels, in which the excitation/detection site is within about 12 cm of the loading site, it is possible to sequence up to 300 nucleotides (nt) in under 20 minutes. This is accomplished through the use of field densities of 100–400 volt/cm which are made possible by the improved heat dissipation which can be obtained using ultra-thin gels. In addition, the voltage may be varied throughout any given sample run in order to allow maximum separation of sample.

Figure 2A:
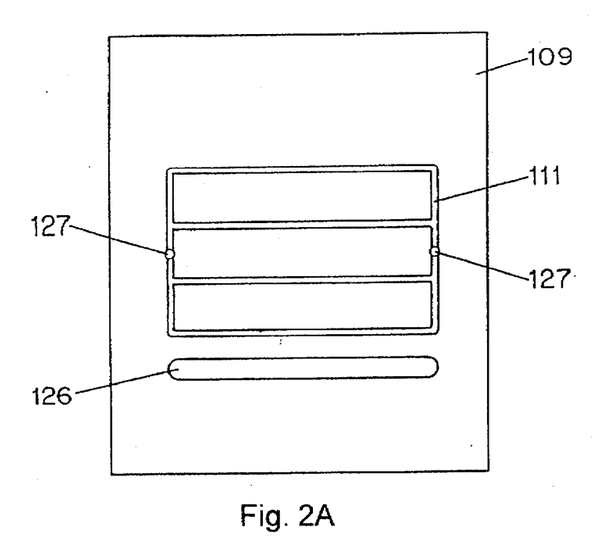
FIG. 2 shows a mounting plate for use in the present invention.
Figure 2B:
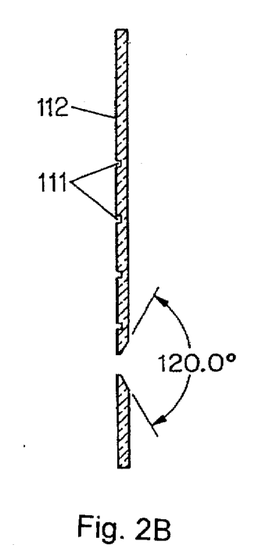

To enhance the heat dissipation which is achieved as a result of the use of thin gels, the present invention preferably makes use of a vacuum mounting technique. In this technique, as shown in FIG. 1, the gel holder 101 is mounted on a thermally conductive ceramic plate, 109, preferably made of alumina. FIG. 2 shows the structure of the mounting plate in more detail. As shown, the plate has an opening 126 cut to align with the detection site 106. This opening is preferably beveled so that it is wider on the side away from the gel mounting surface 112. The gel mounting surface 112 has canal 111 formed in it which is connected to vacuum pump 110 via ports 127 which are connected to tubing 113. The canal 111 is suitably about 0.1 inches wide (e.g. 0.092) and 0.05 inches (e.g. 0.047) deep, and is sealed over by the back substrate of the gel holder, 101, when properly mounted. The tight juxtaposition of the back substrate with the ceramic plate gives improved heat transference when compared to edge clamping devices. Vacuum sealing also allows for exquisite precision in focussing excitation sources, as described below.

A heat sink (not shown) consisting of an aluminum or other heat conducting metal sheet with extended fins may be contacted with the back face of the ceramic plate in order to improve heat conductance away from the gel.

The planar electrophoresis gel 102 generally contains a plurality of lanes for loading and detecting sample across the width of the gel. In many prior art devices, for example the device disclosed in U.S. Pat. No. 4,811,218, detection of various lanes is accomplished using a single detector which moves across the width of the gel and collects data from each lane in series. Because of the rapid progress of sample through the gel which is achieved using the present invention, (under 300 v/cm electric field, there is only about six seconds between oligonucleotides differing by one nucleotide), however, systems which require physical movement of a detector are inadequate to collect the data for each of the lanes. Improvements in the delivery of excitation energy and the detection of emitted energy therefore had to be made as part of the development of an effective apparatus and method for high throughput electrophoretic separations.

Delivery Of Excitation Energy

Figure 3A:
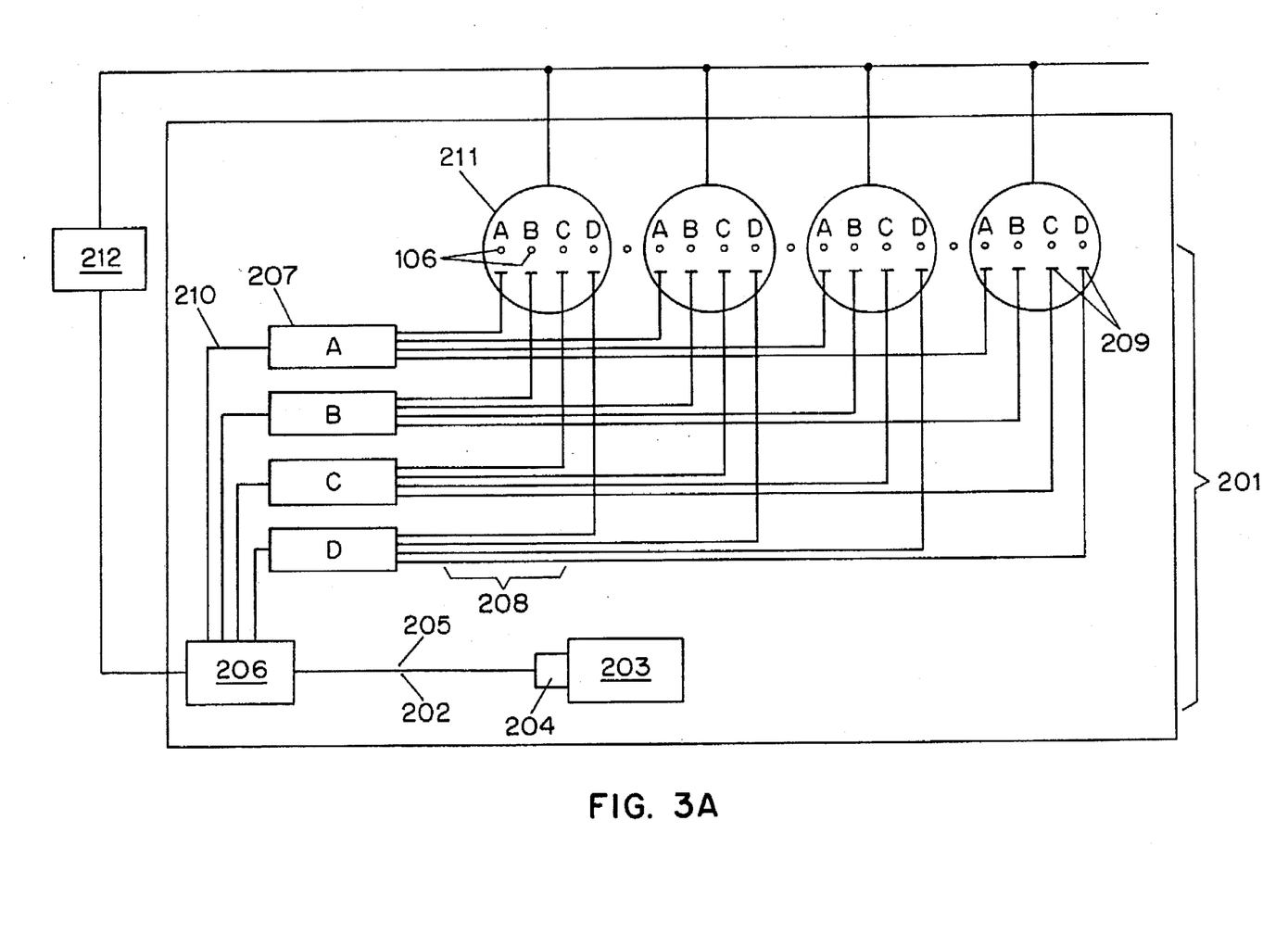
FIGS. 3A and 3B shows excitation and detection systems useful in the present invention.

In one embodiment of the invention, illustrated in FIG. 3A, excitation energy is conveyed to the excitation site by a fixed multiplexed fiber optic array, 201. Radiation, 202, from a source such as a laser, or light emitting diode, 203, is coupled, using a fiber launch or the like, 204, into an optical fiber 205. Suitable optical fibers for this purpose are fibers of 125 microns thickness with a core of 50 microns (if multimode) or preferably a core of 3.7 microns (single mode). The optical fiber carries the beam to a miniature board mountable switch, 206, that permits the switching of an optical signal from one output fiber 210 to another. For example, optical switching can be accomplished using a switch available from AMP, Inc., Harrisburg, Pa., in which a slight pivoting motion of a spherical mirror reflects the optical signal into one of two output fibers. The switch takes approximately 5–10 milliseconds to settle after each change. Several switches can be used in combination permitting the excitation beam to be divided into any number of output optical fibers 210.

As shown in FIG. 3A, four output fibers 210 are used to permit the sequential excitation of four groups of excitation/detection sites. The use of four output fibers is merely exemplary, however. In general, the apparatus of the invention will divide the incident light into from 2 to 10 groups.

Light in each output fiber 210 is conducted by the output optical fiber 210 to a beam splitter 207A, 207B, 207C or 207D which separates the beam into a plurality of final optical fibers 208, each conducting its respective fraction of the input excitation beam as an excitation beamlet. Each of the split optical fibers conveys the beamlet to a SELFOC® rod gradient index (GRIN) lens 209 (NSG America, Inc.; Somerset NJ) which is fixed in location and disposed to irradiate its respective excitation site, 106, one lens for each excitation site. Experimental evidence shows that use of the vacuum seal to mount the gel holder also provides the advantage that the focal length of the GRIN lens can be exquisitely positioned with respect to the ultra-thin gel. The vacuum seal holds the gel extremely flat against the ceramic plate without the slight bowing or bending of gel holders found in edge clamped apparatuses.

The final optical fibers 208 and the lenses 209 are disposed to form a linear array of detection sites. Within this array, the final optical fibers 208 are ordered so that, when using four groups of excitation signals, every fourth detection belongs to the same group. The effect is that only a sub-set of excitation sites are irradiated at any one time (A, B, C, or D). Of course, if one were using two groups of excitation signals (only a single split of the incident beam 202), the final optical fibers 208 would be arranged in an alternating pattern (see FIG. 3B). This provides the advantage that a single detector, 211, may be employed to detect emissions from a plurality of excitation/detection sites if the detector output is synchronized with the switch so as to allow the signal processor to identify which signal came from which excitation/detection site.

The optical switch, 206, is programmed to switch the input laser beam into each of the output fibers 210 (and thus into the final optical fibers 208), for a period of preferably 20–100 milliseconds. Synchronization of the switch and detectors may be obtained with a microprocessor, 212.

The fixed multiplexed fiber optic array permits a high number of data points per second to be taken from each lane of the gel by conveying pulsed irradiation to each excitation site. Further, it permits use of a reduced number of detectors.

Figure 3B:
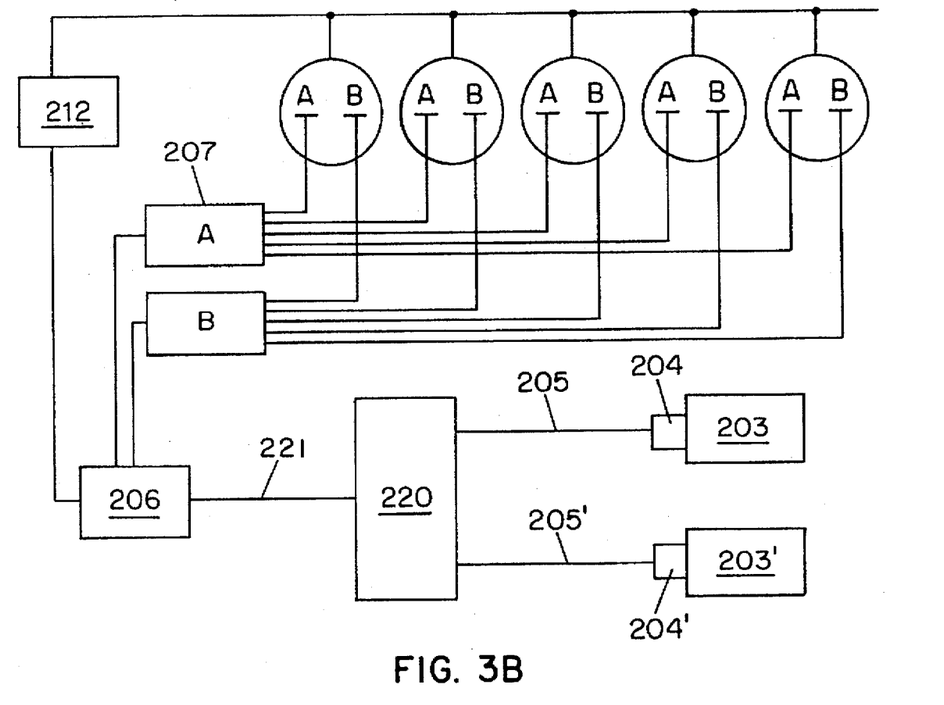

The fixed multiplexed fiber optic array can also be modified to bring different irradiation sources to the same excitation site in a series of alternating pulses as shown in FIG. 3B. Such an arrangement is constructed by employing different excitation sources 203 and 203', each coupled to an optical fiber 205 and 205'. An optical switch 220, operating in the opposite direction to switch 206 is employed to alternately select which source is to be conducted to the optical switch 206 via optical fiber 221. This arrangement permits multicolor fluorescence imaging for use when more than one fluorophore is used in any given lane of the gel.

Figure 4:
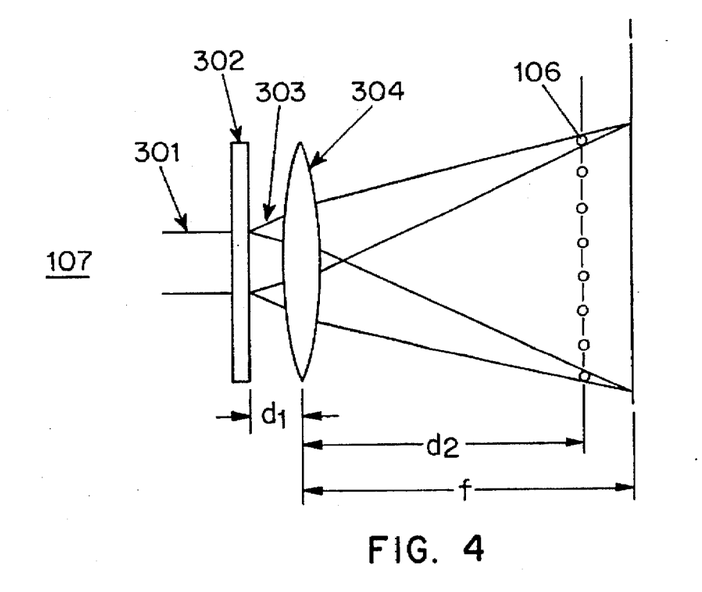
FIG. 4 shows a spot array generating grating system useful in the present invention.

In a second embodiment of the invention, illustrated in FIG. 4, radiation 301 from an excitation source 107 is directed to the excitation site 106 by use of a multiple beam splitter 302, such as a Spot Array Generation Grating which splits the incident beam into a number of beamlets, generally from 2 to 24 beamlets. In the illustrated embodiment, an incident laser beam of a frequency suitable for excitation of the fluorophore is directed into a binary phase grating, approximately 1 cm square, mounted on glass, thermoplastic or the like of approximately 1/8th inch thickness (Semiconductor Technology Inc, Pointe Claire, Quebec). The transmitted beam is divided into a linear array of the desired number of excitation beamlets, 303, one for each intended excitation site, 106. The beamlets are directed to a focussing lens, 304 (e.g., Stock #G69,129, Catalog 1994, Edmund Scientific). The focussing lens has a focal distance, f, of 505 mm in the preferred embodiment. The spot at each excitation site can be varied in size by changing the distance, d, between the lens and the excitation site. In the preferred embodiment, spots are between 0.1 mm and 0.2 mm diameter. In the preferred embodiment, the spot array generation grating divides the incident laser beam into a linear array of 16 spots, and the lens is disposed between 200 to 500 mm from the gel.

As will be apparent to those skilled in the art, any excitation source can be used in embodiments utilizing a fiber optic array or a spot array generating grating, provided that the source is matched with the fluorophore to be used so that the radiation from the source excites the fluorophore to stimulate emission of detectable radiation. For example, the following non-limiting examples of commercially available excitation sources can be employed in the present invention: Optical lasers, e.g., Argon ion lasers, Argon krypton mixed gas lasers, Helium-neon lasers and doubled YAG lasers; Laser Diodes; Fiber (Solid State) Lasers; and Blue, Green, Red or infra red-Light Emitting Diodes (LEDs).

Figures 5, 6:
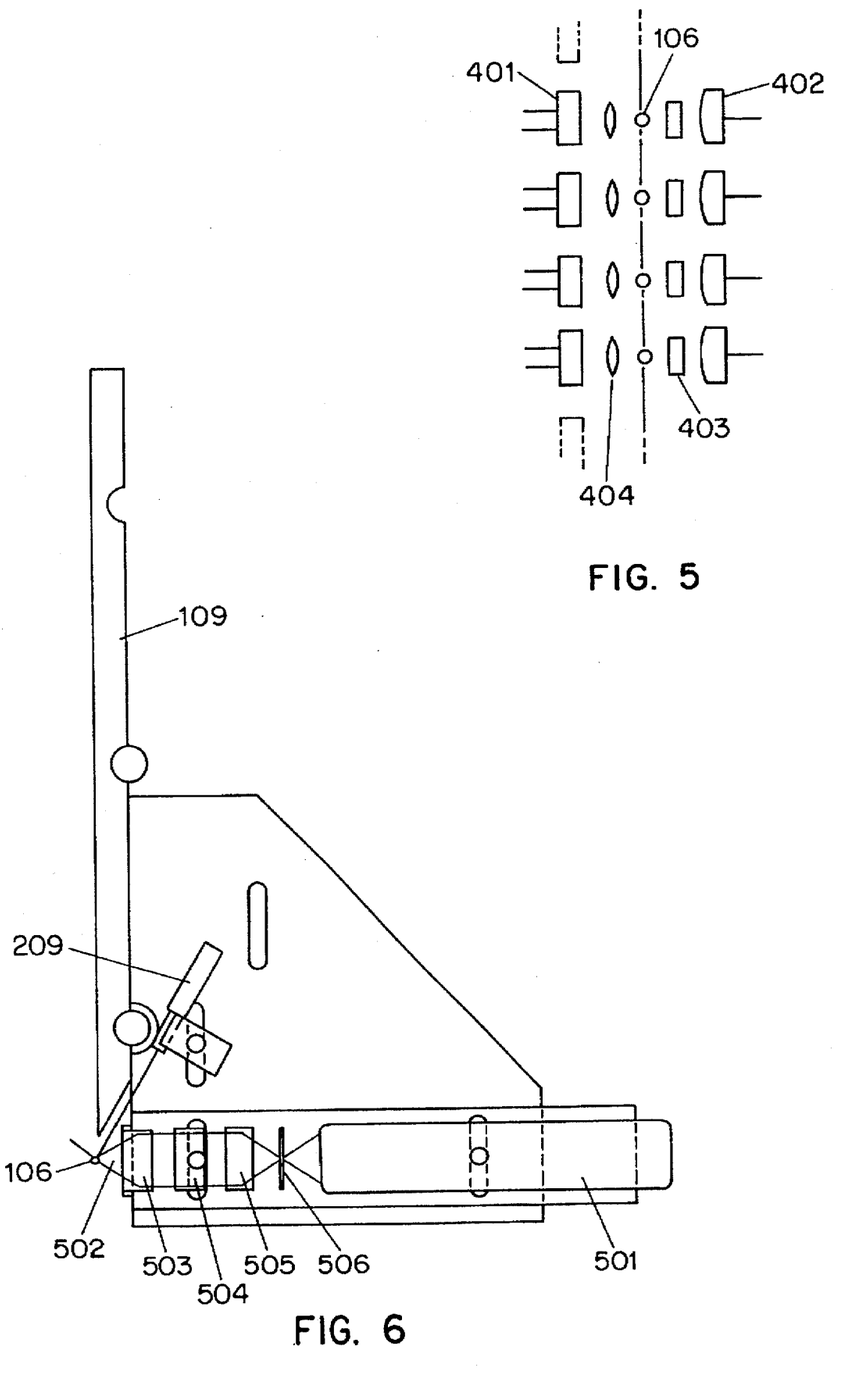
FIG. 5 shows an excitation and detection system employed in one embodiment of the present invention.
FIG. 6 shows a detection system useful in the present invention.

In a third embodiment of the invention, illustrated in FIG. 5, an independent excitation source is used for each excitation site. An effective and extremely low cost excitation source for this purpose is a light emitting diode for example those available from Stanley Corp. and identified as Type No. AN, BN, CN or DN. Unlike lasers, LEDs emit light in a broad band spectrum. Bandpass filters 403 disposed between the excitation/detection site 106 and the detector 402 should therefore be carefully selected to eliminate as much overlapping excitation irradiation from the detector as possible. One LED, 401, is disposed to irradiate each excitation site, 106, with or without a focussing lens 404 to focus the emitted radiation. An LED can emit 1.5–15 mW, sufficient to excite a population of fluorophores. In this embodiment, using an infra-red LED with Cy8 or Cy9 as a fluorophore, where the emitted light is in the infra-red region, the detector is preferably a photodiode detector 402.

While it is possible to have each LED 401 in the array constantly illuminated such that data collection from each lane can be continuous, it may be advantageous to use a pulsed excitation source in this embodiment as well. For example, where the lanes are close together, pulsing alternate lanes, or every fourth lane, may improve the accuracy of the detector by eliminating carry over form one lane to the next.

Fluorophores useful in the present invention are those which can be coupled to organic molecules, particularly proteins and nucleic acids and which emit a detectable amount of electromagnetic radiation in response to excitation by an available excitation source. As used herein, the term fluorophore encompasses materials having both fluorescent and phosphorescent emissions. It is desirable that the fluorophore exhibit a sufficient Stokes shift to permit filtering of emitted radiation from the excitation irradiation. A further limiting factor on the choice of fluorophore is whether the fluorophore contains functional groups that prevent it from surviving intact during the cleavage and deprotection reactions of commercially available oligonucleotide synthesis.

Suitable fluorophores for this invention include fluorescein and its analogs, rhodamine and its analogs, cyanine and related polymethines and their analogs, and the like. Specific fluorophores which suitable for use with the present invention are Fluorescein isothiocyanate (FITC); 4-fluoro-7-nitrobenzofurazan (NBD-F); Texas Red® (Molecular Probes, Inc.; Eugene, Oreg.); tetramethyl rhodamine isothiocyanate (TRITC); and Cyanine dyes, especially, Cy5, Cy 5.5 Cy7, Cy7.5, Cy8 and Cy9 (Biological Detection Systems, Pittsburgh, Pa.). Fluorescein fluorophores are preferably excited using an argon ion laser, while rhodamine fluorophores are preferably excited using a helium neon laser. The cyanine dyes, which are described in U.S. Pat. Nos. 4,981, 977 and 5,268,486, which are incorporated herein by reference, are useful in combination with a red or infrared LED excitation source because the cyanine fluorophores Cy5 to Cy9 absorb and emit in the red and infra-red regions or laser diodes. Infra-red emissions are detected preferably with photodiodes, and particularly silicon photodiodes, 402, rather than PMTs.

An alternative to using LEDs in the above embodiment is use of laser diodes. Red and infra-red laser diodes can be used to excite fluorophores such as Cy5, Cy5.5, and Cy7.

Detection of Fluorophore Emitted Radiation

Emissions from the fluorophores are detected by a detector disposed to receive radiation from the detection site.

FIG. 6 illustrates a first embodiment, particularly suited for use with a fixed multiplexed fiber optic array. A linear array of detectors 501, is disposed to receive emissions 502, from a linear array of detection sites 106. A detector may be any two dimensional detector, such as a CCD, a photodiode or, in the preferred embodiment, a photomultiplier tube (PMT). Disposed between the detection site and the PMT are a collecting lens 503, a bandpass filter 504, a focussing lens 505, and a spatial filter 506. The bandpass filter is an interference filter (Omega Optical, Inc. Brattleboro, Vt.) or the like of 20 to 40 nm transmission wavelength width chosen to transmit the fluorescence emission and to block reflected light of the excitation source. The spatial filter is chosen to optimize recognition of the band of fluorophore-labeled sample as it passes through the detection site. Elimination of fringes and tails of bands using a spatial filter tends to increase the signal to noise ratio of the detected signal. Preferred spatial filters are rectangular in shape with a height of 100 microns and width of 250 microns.

The detector collects a signal, which is integrated over a finite time-span and converted to a digital output. A suitable integration time for the invention is 5–100 milliseconds. When a PMT is used to record a plurality of excitation/detection sites, the width of the PMT is selected in a manner consistent with the number of sites. In general, PMT's with width of from 3–15 mm, and preferably about 5 mm are suitable. In this case, the integration of signal must be synchronized with the multiplexing switch of the excitation irradiation source. Such synchronization can be controlled by a microprocessor 212. As stated above, a suitable period of multiplex switching is 20–100 milliseconds, although any period that results in a sufficient number of data points for analysis can be used. Fluorescence emissions can therefore be correlated with the respective detection site on the gel. Fluorophore must be chosen such that the delay in fluorescence emission from an old detection site does not cause significant overlap with the new fluorescence emissions from a new detection site.

Figure 7:
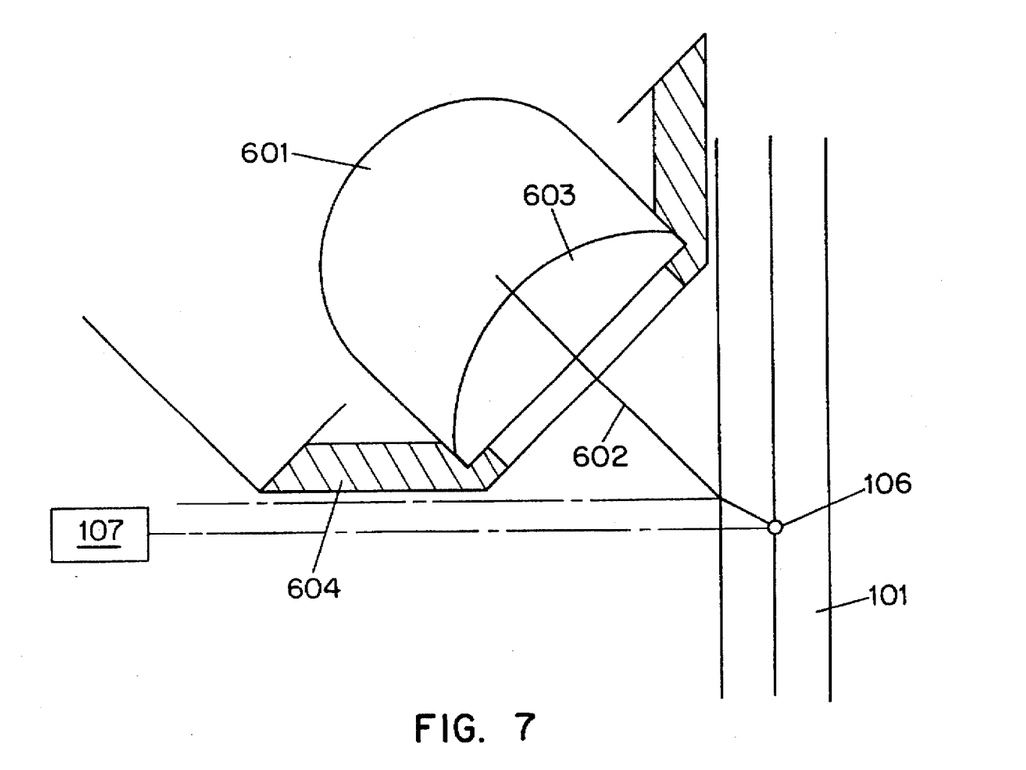
FIG. 7 shows an alternative detection system useful in the present invention.
Figure 8A:
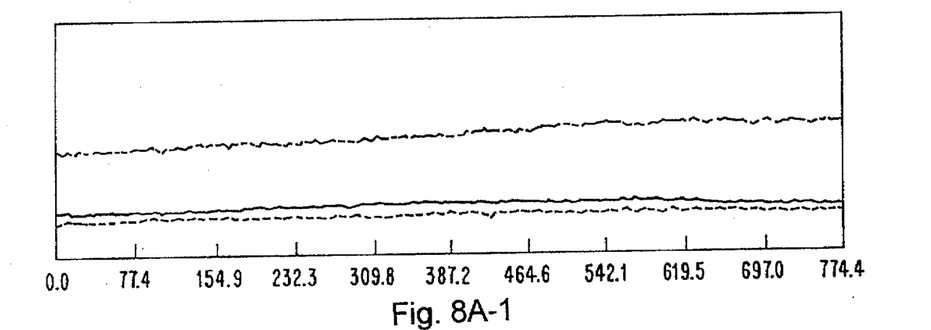
FIGS. 8A–8E shows the output of a photomultiplier tube when sequencing M13 using an apparatus of the invention.
Figure 8A:
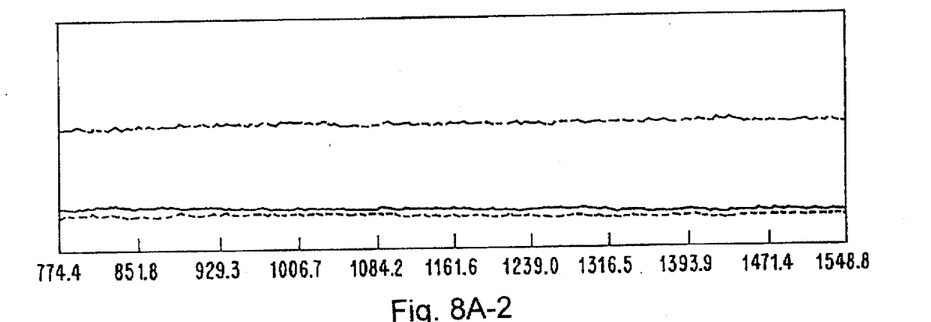
Figure 8A:
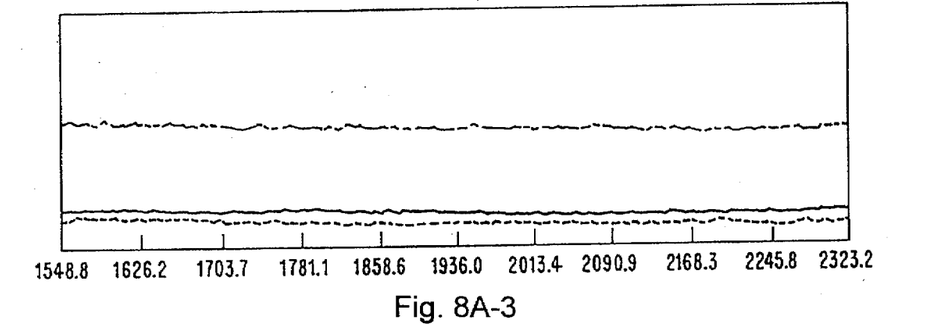
Figure 8A:
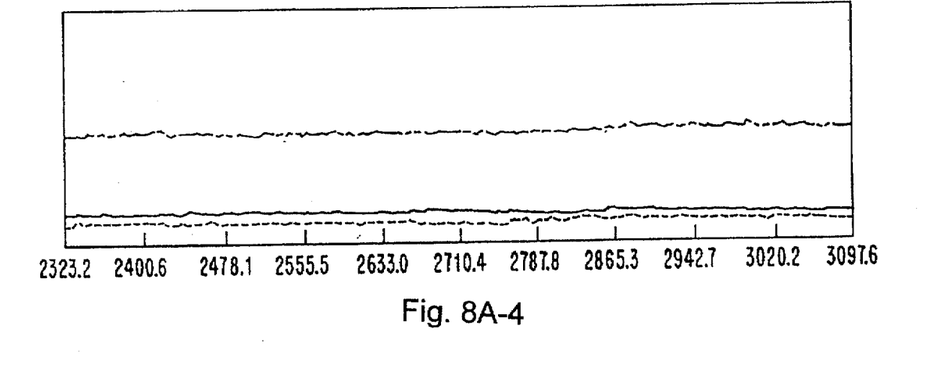
Figure 8B:
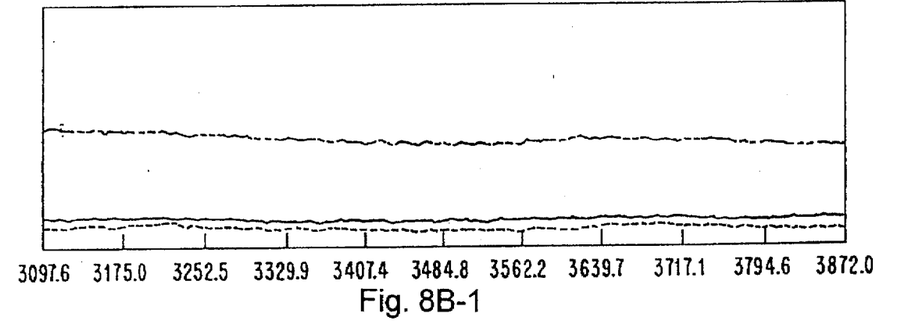
Figure 8B:
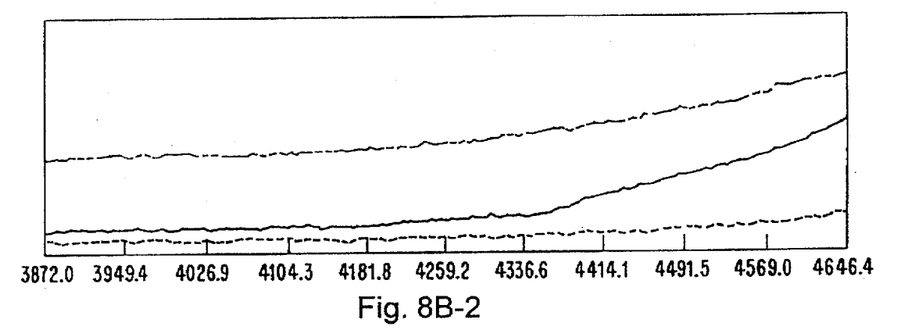
Figure 8B:
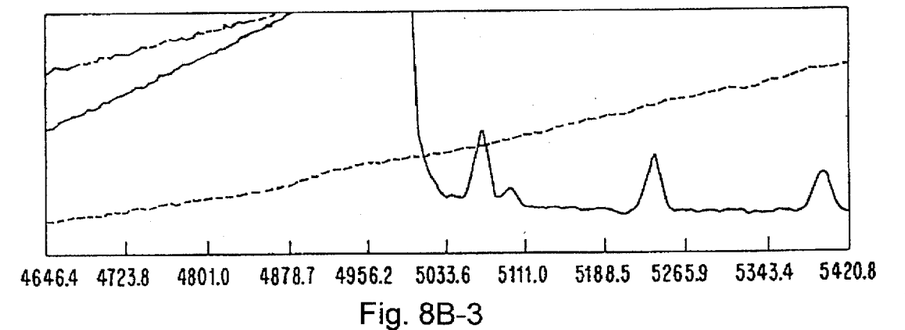
Figure 8B:
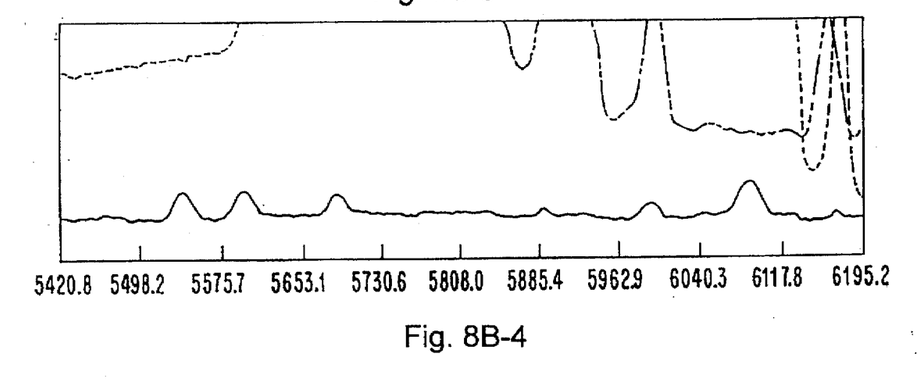
Figure 8C:
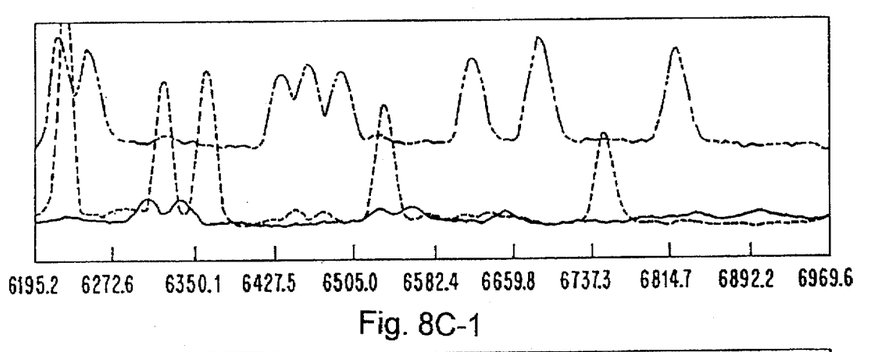
Figure 8C:
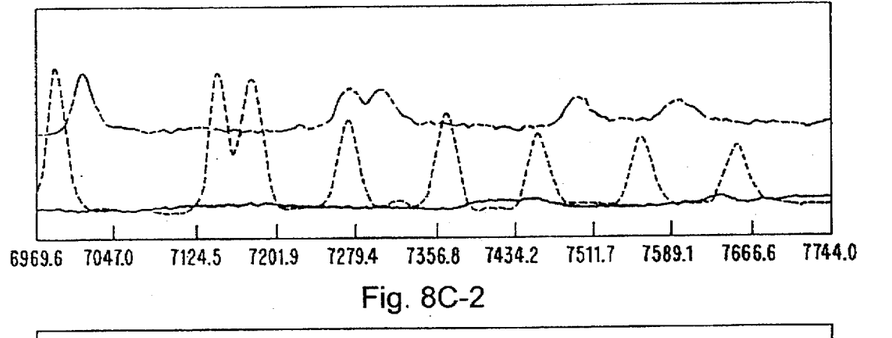
Figure 8C:
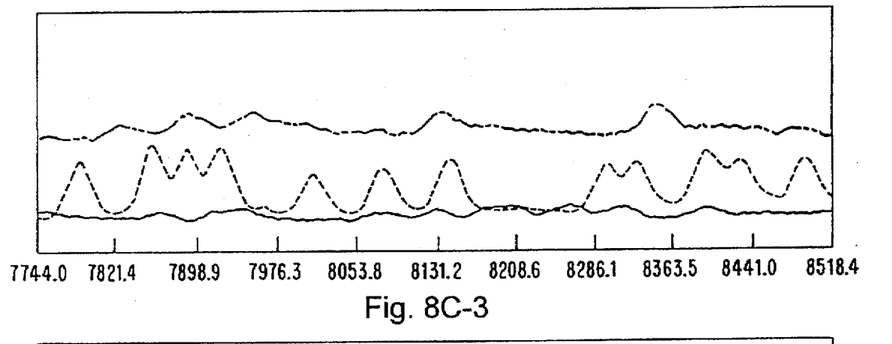
Figure 8C:
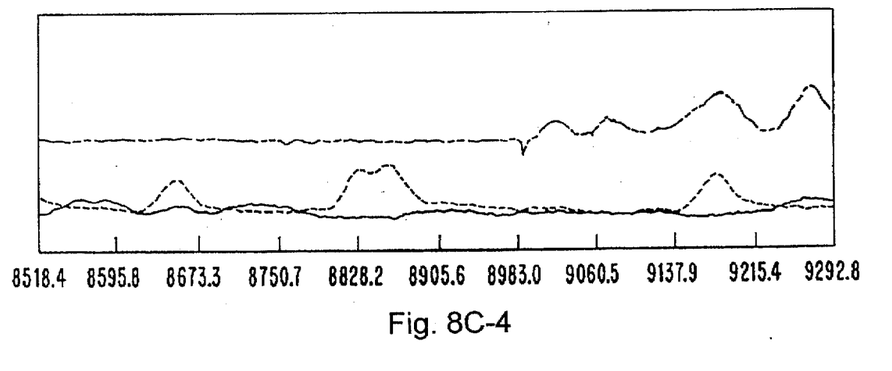
Figure 8D:
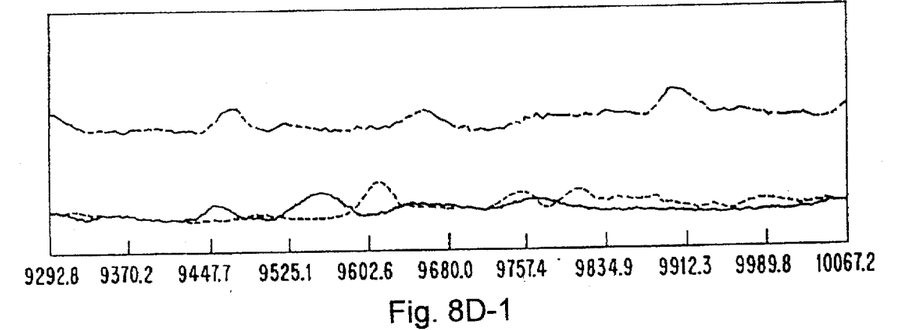
Figure 8D:
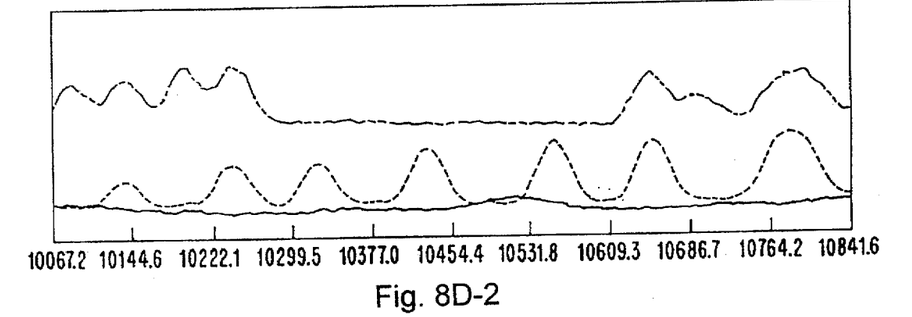
Figure 8D:
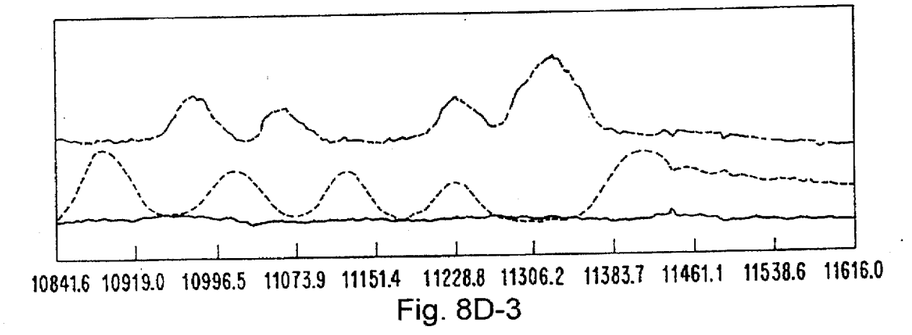
Figure 8D:
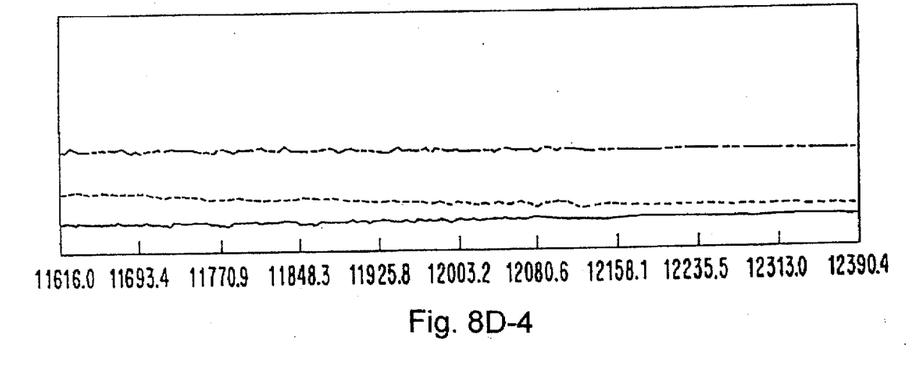
Figure 8E:
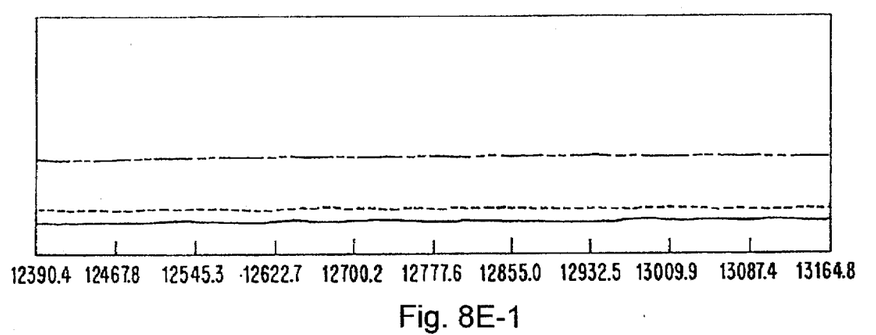
Figure 8E:
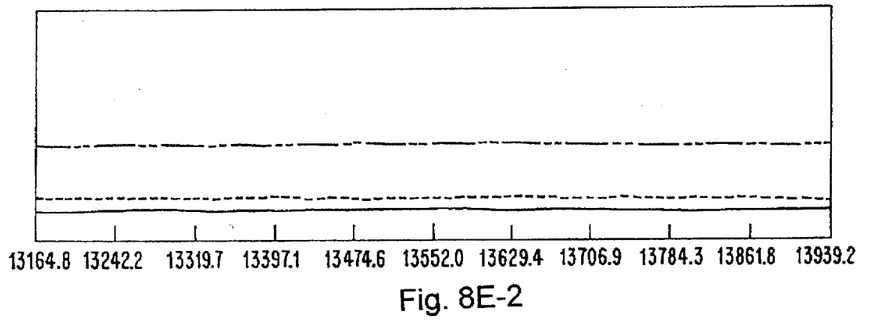
Figure 8E:
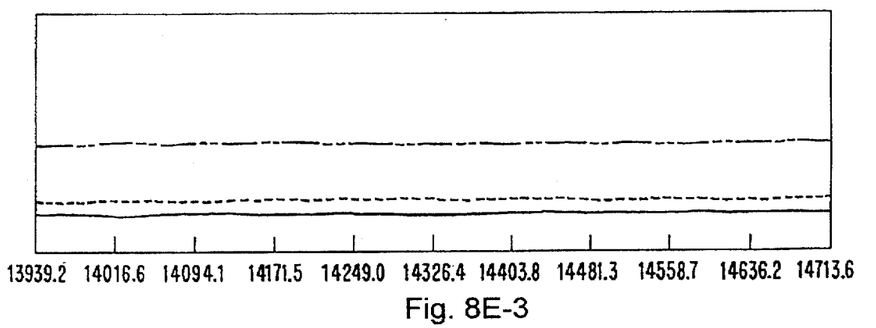
Figure 8E:
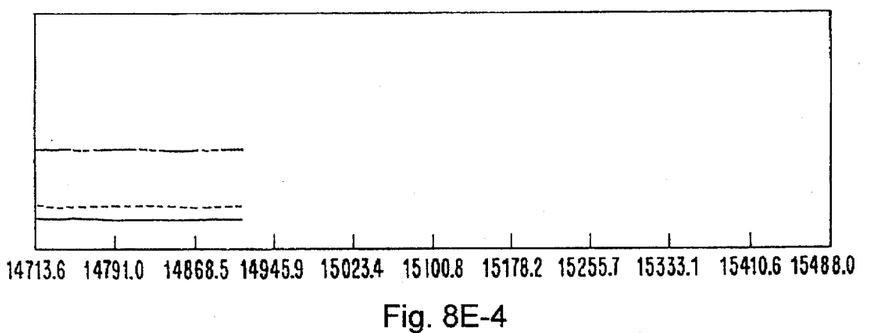

In another embodiment, if multiplexed excitation beams are not used, then a single detector is required for each detection site. Any type of detector may be employed, such as CCDs, PMTs or silicon photodiodes (Series S2386 or S2387; Hamamatsu Photonics KK, Hamamatsu City, Japan). The silicon photodiode 601 is disposed at the focal distance of the lens of the diode 603 from the apparent detection site 106 and to collect emitted light 602 off of the horizontal axis of the gel, as illustrated in FIG. 7. The irradiation source 107 is directed to the excitation site along the horizontal axis of the gel. A linear array of detectors can be positioned both above and below said axis in diode holders 604. Thus, if a first linear array of detectors is focussed at excitation sites staggered from the excitation sites recorded by the second linear array of detectors, it is possible to utilize twice as many excitation spots per gel. Further, a linear array of detectors may be disposed on the opposite side of the gel, again above or below the horizontal axis of the gel. If all detectors detect excitation sites staggered from each other, it is possible to detect at least four excitation sites for every unit of detector width.

All signals received from detectors are preferably converted from analog to digital and conveyed to a serial port for transmission to a multipurpose computer for storage and for further processing and analysis. It will be understood, however, that the analog output could be sent directly to an output device for display or printing.

EXAMPLE

A single stranded M13 DNA molecule is hybridized to FITC labelled universal primer. Sequencing reactions are undertaken using SEQUENASE tm in the recommended reaction buffers. After completion of reactions, loading buffer of xylene cyanol, bromophenol blue and glycerol is added to the reaction tubes to provide a visible loading marker. A microgel, prepared as disclosed in U.S. patent application 08/332,577 is mounted on an alumina plate by vacuum seal. A solution electrode is affixed such that the upper chamber contacts the upper end of the gel, and the lower chamber contacts the lower end of the gel. GRIN lenses, each attached to its respective optical fiber of a fiber optic array are disposed at the focal length from the excitation site near the lower end of the gel. An argon ion laser of 5 mW power output, 488 nm wavelength is directed into the optical fiber by the fiber launch (upstream from the beam splitter). A linear array of PMTs is disposed to receive fluorescence emissions from the detection sites, one PMT per detection site. The M13 sample is loaded into the loading site. An electric field of 250 v/cm is suspended across the gel. Electrophoresis of the sample through the gel is recorded and displayed as in FIGS. 8A–8E, where the x-axis shows time in tenths of seconds. The data shows clearly resolved M13 sequence data out to 220 nt in 12 minutes.

We claim:

1. An apparatus for electrophoretic separation and detection of a plurality of samples, each labeled with a fluorophore and loaded into a lane of an electrophoresis gel, comprising:
   (a) a housing adapted to receive an electrophoresis gel holder containing an electrophoresis gel loaded with the samples;
   (b) an excitation source for providing an incident beam of coherent radiation of a frequency suitable for excitation of the fluorophore,
   (c) a spot array generation grating for dividing the incident beam of coherent radiation into a plurality of excitation beamlets of the frequency suitable for excitation of the fluorophore and directing each excitation beamlet to an excitation/detection site on a different lane of the electrophoresis gel; and
   (d) at least one detector for detecting emissions from the excitation/detection sites.

2. An apparatus according to claim 1, wherein the detector is a photodiode.

3. An apparatus according to claim 1, further comprising a thermally conductive mounting plate and means for vacuum affixing the gel holder to the mounting plate.

4. An apparatus according to claim 3, wherein the mounting plate is formed from a ceramic.

5. An apparatus according to claim 4, wherein the mounting plate is alumina.

6. An apparatus according to claim 1, further comprising a power supply for providing an electric field of 100–400 V/cm to an electrophoresis gel placed in the apparatus.

7. An apparatus according to claim 1, wherein the excitation source is a laser.

8. An apparatus according to claim 1, wherein the excitation source is an argon ion laser.

9. An apparatus according to claim 1, wherein the excitation source is a helium neon laser.

10. An apparatus according to claim 1, wherein the excitation source is a laser diode.

11. An apparatus according to claim 1, wherein the grating divides the incident beam into 8 to 24 beamlets.

12. An apparatus in accordance with claims 11, wherein the grating divides the incident beam into 16–24 beamlets.

13. An apparatus according to claim 12, wherein the grating divides the incident beam into 16 beamlets.

14. An apparatus according to claim 12, wherein the grating divides the incident beam into 24 beamlets.

15. An apparatus according to claim 1, wherein the housing holds a gel holder disposed therein in a fixed position relative to the spot array generation grating and the means for detecting emissions.

\* \* \* \* \*